US00PP27110P2

(12) United States Plant Patent
Meinl

(10) Patent No.: US PP27,110 P2
(45) Date of Patent: Aug. 30, 2016

(54) ***HYDRANGEA* PLANT NAMED 'HORCOS'**

(50) Latin Name: *Hydrangea macrophylla*
Varietal Denomination: Horcos

(71) Applicant: Katrin Meinl, Dresden (DE)

(72) Inventor: Katrin Meinl, Dresden (DE)

(73) Assignee: Kühne Jungpflanzen Claus + Torsten Kühne Gbr, Dresden (DE)

( * ) Notice: Subject to any disclaimer, the term of this patent is extended or adjusted under 35 U.S.C. 154(b) by 98 days.

(21) Appl. No.: 14/120,667

(22) Filed: Jun. 14, 2014

(51) Int. Cl.
*A01H 5/02* (2006.01)

(52) U.S. Cl.
USPC ..... Plt./250

(58) Field of Classification Search
USPC ..... Plt./250
See application file for complete search history.

(56) References Cited

PUBLICATIONS

UPOV hit on *Hydrangea* 'Horcos', QZ PBR grant No. 38262, publication date Dec. 15, 2011.*

* cited by examiner

*Primary Examiner* — Anne Grunberg
(74) *Attorney, Agent, or Firm* — C. A. Whealy

(57) ABSTRACT

A new and distinct cultivar of *Hydrangea* plant named 'Horcos', characterized by its upright and mounded plant habit; moderately vigorous growth habit; strong stems; and large mophead-type inflorescences with light red purple-colored sterile flowers with darker red purple-colored margins.

2 Drawing Sheets

Botanical designation: *Hydrangea macrophylla.*
Cultivar denomination: 'HORCOS'.

BACKGROUND OF THE INVENTION

The present invention relates to a new and distinct cultivar of *Hydrangea* plant, botanically known as *Hydrangea macrophylla* and hereinafter referred to by the name 'Horcos'.

The new *Hydrangea* plant is a product of a planned breeding program conducted by the Inventor in Dresden, Germany. The objective of the breeding program was to develop new container-type *Hydrangea* plants with strong stems and attractive leaf, stem and flower coloration.

The new *Hydrangea* plant originated from a cross-pollination in 2004 of *Hydrangea macrophylla* 'Selma', not patented, as the female, or seed parent and a proprietary selection of *Hydrangea macrophylla* identified as code number 41-99/1, not patented, as the male, or pollen, parent. The new *Hydrangea* plant was discovered and selected by the Inventor in May, 2006 as a flowering plant within the progeny of the stated cross-pollination in a controlled environment in Dresden, Germany.

Asexual reproduction of the new cultivar by softwood cuttings in Dresden, Germany since June, 2006 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Horcos'. These characteristics in combination distinguish 'Horcos' as a new and distinct *Hydrangea* plant:

1. Upright and mounded plant habit.
2. Moderately vigorous growth habit.
3. Strong stems.
4. Large mophead-type inflorescences with light red purple-colored sterile flowers with darker red purple-colored margins.

Plants of the new *Hydrangea* differ primarily from plants of the female parent, 'Selma', in the following characteristics:

1. Plants of the new *Hydrangea* have stronger stems than plants of 'Selma'.
2. Plants of the new *Hydrangea* have larger inflorescences than plants of 'Selma'.

Plants of the new *Hydrangea* differ primarily from plants of the male parent selection in the following characteristics:

1. Plants of the new *Hydrangea* are more vigorous than plants of the male parent selection.
2. Plants of the new *Hydrangea* have larger inflorescences than plants of the male parent selection.
3. Plants of the new *Hydrangea* and the male parent selection differ in flower color as plants of the male parent selection have red-colored flowers.

Plants of the new *Hydrangea* can be compared to plants of *Hydrangea macrophylla* 'Hbachi', not patented. Plants of the new *Hydrangea* differ primarily from plants of 'Hbachi' in the following characteristics:

1. Leaves of plants of the new *Hydrangea* are darker green in color than leaves of plants of 'Hbachi'.
2. Plants of the new *Hydrangea* have larger sterile flowers than plants of 'Hbachi'.

3. Plants of the new *Hydrangea* and 'Hbachi' differ slightly in flower color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Horcos' grown in a container.

The photograph on the second sheet is a close-up view of a typical inflorescence of 'Horcos'.

DETAILED BOTANICAL DESCRIPTION

Plants used in the aforementioned photographs and in the following description were grown in 13-cm containers in a glass-covered greenhouse in Dresden, Germany and under cultural conditions typical of commercial *Hydrangea* production conditions. Plants of the new *Hydrangea* were two years old when the photographs and description were taken. During the production of the plants, day temperatures ranged from 18° C. to 25° C. and night temperatures ranged from 16° C. to 17° C. In the following description, color references are made to The Royal Horticultural Society Colour Chart, 2007 Edition, except where general terms of ordinary dictionary significance are used.

Botanical description: *Hydrangea macrophylla* 'Horcos'.

Parentage:

*Female, or seed, parent.*—*Hydrangea macrophylla* 'Selma', not patented.

*Male, or pollen, parent.*—Proprietary selection of *Hydrangea macrophylla* identified as code number 41-99/1, not patented.

Propagation:

*Type cutting.*—By softwood cuttings.

*Time to initiate roots, summer.*—About 14 days at temperatures about 18° C.

*Time to initiate roots, winter.*—About 16 days at temperatures about 18° C.

*Time to produce a rooted young plant, summer.*—About 28 days at temperatures about 18° C.

*Time to produce a rooted young plant, winter.*—About 30 days at temperatures about 18° C.

*Root description.*—Medium in thickness, fibrous; white to grey in color.

*Rooting habit.*—Moderately freely branching; medium density.

Plant description:

*Plant and growth habit.*—Perennial subshrub; upright and mounded plant habit; broadly inverted triangle; freely branching habit with about six lateral branches developing per plant; strong lateral branches; moderately vigorous growth habit.

*Plant height.*—About 28.2 cm.

*Plant diameter or area of spread.*—About 40.6 cm.

*Lateral branches.*—Length: About 17.8 cm. Diameter: About 5 mm. Internode length: About 3.2 cm. Texture: Smooth, glabrous. Strength: Strong. Aspect: About 45° from vertical. Color, developing: Close to 143C; at the nodes, slightly tinged with close to N186C. Color, developed: Close to between 199A and N199B. Lenticels: Density: Moderate. Length: About 1 mm. Diameter: About 0.75 mm. Color: Close to N186C.

Leaf description:

*Arrangement.*—Opposite, simple.

*Length.*—About 12 cm.

*Width.*—About 7.8 cm.

*Shape.*—Elliptic-oblong to obovate to a ovate.

*Apex.*—Apiculate.

*Base.*—Attenuate.

*Margin.*—Serrate.

*Texture, upper surface.*—Glabrous; rugose.

*Texture, lower surface.*—Glabrous; slightly rugose.

*Venation pattern.*—Pinnate.

*Color.*—Developing leaves, upper surface: Close to N137D; towards the margins, strongly tinged with close to 200A. Developing leaves, lower surface: Close to 147B. Fully expanded leaves, upper surface: Darker than between N137A and 147A; venation, close to 144A. Fully expanded leaves, lower surface: Close to 147B; venation, close to 144A to 144B.

*Petioles.*—Length: About 2.2 cm. Diameter: About 4 mm. Texture, upper and lower surfaces: Smooth, glabrous. Color, upper and lower surfaces: Close to 144A.

Inflorescence & flower description:

*Flower type and habit.*—Single sterile and inconspicuous fertile flowers arranged on terminal mophead-type panicles; panicles flattened globular in overall shape; fertile flowers face mostly upright and sterile flowers face upright to outwardly.

*Fragrance.*—Faintly fragrant, pleasant.

*Natural flowering season.*—Continuous flowering from late spring to late summer in The Netherlands.

*Flower longevity, fertile flowers.*—Flowers last about one week on the plant; flowers not persistent.

*Flower longevity, sterile flowers.*—Flowers last about six weeks on the plant; flowers persistent.

*Quantity of flowers.*—Freely flowering; about 65 fertile flowers and about 125 sterile flowers per panicle.

*Panicle height.*—About 12.4 cm.

*Panicle diameter.*—About 16.7 cm.

*Flower diameter, fertile flowers.*—About 9 mm.

*Flower depth (height), fertile flowers.*—About 5 mm.

*Flower diameter, sterile flowers.*—About 5.1 cm.

*Flower depth (height), sterile flowers.*—About 1.2 cm.

*Flower buds, fertile flowers.*—Length: About 4 mm. Diameter: About 4 mm. Shape: Globular. Color: Close to 144D.

*Flower buds, sterile flowers.*—Length: About 1 cm. Diameter: About 8 mm. Shape: Ovoid. Color: Close to 140D; margins, close to 58B.

*Petals, fertile flowers only.*—Quantity and arrangement: Five in a single whorl. Length: About 3 mm. Width: About 1.75 mm. Shape: Ovate, concave. Apex: Acute. Base: Cuneate. Margin: Entire. Texture, upper and lower surfaces: Smooth, glabrous. Color: When opening and fully opened, upper surface: Close to 75B. When opening and fully opened, lower surface: Close to 75C.

*Sepals, fertile flowers.*—Quantity and arrangement: Five in a single whorl. Length: About 1.5 mm. Width: About 1 mm. Shape: Deltoid. Apex: Acute. Base: Broadly cuneate. Margin: Entire. Texture, upper and lower surfaces: Smooth, glabrous. Color, upper and lower surfaces: Close to 144B.

*Sepals, sterile flowers*.—Quantity and arrangement: Four, occasionally five, in a single whorl. Length: About 2.6 cm. Width: About 3.2 cm. Shape: Broadly rhomboidal to reniform. Apex: Broadly and bluntly acute. Base: Broadly cuneate. Margin: Entire. Texture, upper and lower surfaces: Smooth, glabrous. Color: When opening, upper and lower surfaces: Center, close to 150D; towards the margins, close to 53D and 58B. Fully opened, upper surface: Center, close to 62C and 73C; towards the margins, close to 59D; with development, center color becomes closer to 65A to 65C and towards the margins, close to 61C to 61D. Fully opened, lower surface: Center, close to 73C to 73D; towards the margins, close to 60D; with development, center color becomes closer to 62B and 63B and towards the margins, close to 63B.

*Pedicels, fertile flowers*.—Angle: About 20° from vertical. Strength: Moderately strong. Length: About 4 mm. Diameter: About 1 mm. Texture: Smooth, glabrous. Color: Close to 63C.

*Pedicels, sterile flowers*.—Angle: About 40° from lateral branch. Strength: Strong. Length: About 2.3 cm. Diameter: About 1.5 mm. Texture: Smooth, glabrous. Color: Close to 68D and marbled with close to 63B.

*Reproductive organs, fertile flowers only*.—Stamens: Quantity per flower: About eight. Filament length: About 4.5 mm. Filament color: Close to NN155D. Anther length: About 0.5 mm. Anther shape: Broadly reniform. Anther color: Close to 157A. Pollen amount: Moderate. Pollen color: Lighter than 156D. Pistils: Pistil quantity per flower: About three. Pistil length: About 1.5 mm. Stigma shape: Club-shaped. Stigma color: Close to NN155A. Style length: About 1 mm. Style color: Close to NN155D. Ovary color: Close to 157D.

*Seeds and fruits*.—Seed and fruit development have not been observed on plants of the new *Hydrangea* to date.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures in USDA Hardiness Zones 5 to 9.

It is claimed:

1. A new and distinct *Hydrangea* plant named 'Horcos' as illustrated and described.

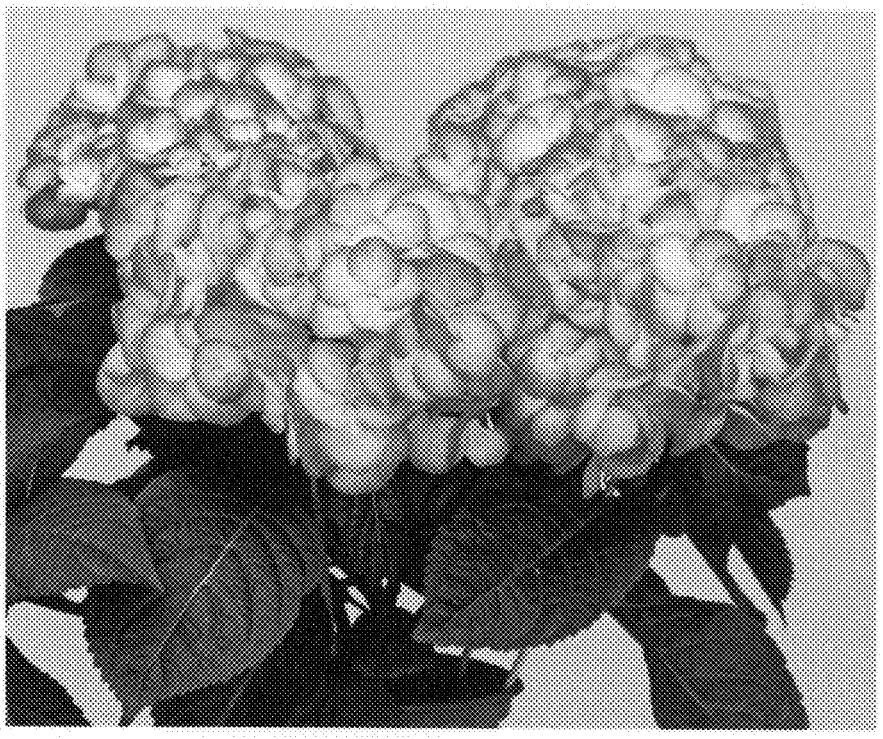

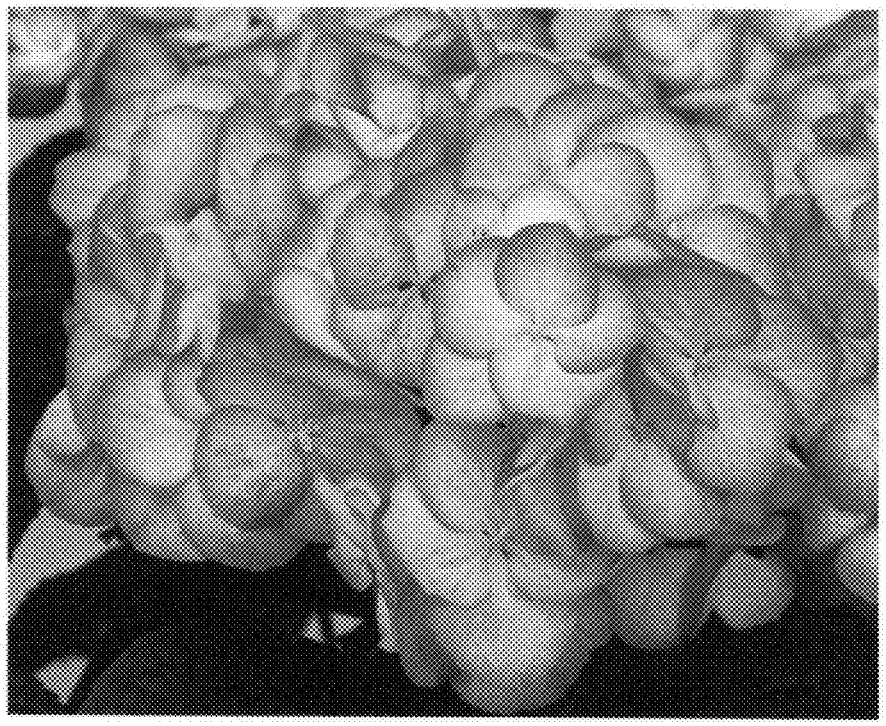

* * * * *